United States Patent [19]

Curlee

[11] 4,178,923
[45] Dec. 18, 1979

[54] THERAPEUTIC CORSET

[76] Inventor: James D. Curlee, 347 Rivermoor Dr., Marietta, Pa. 17547

[21] Appl. No.: 835,868

[22] Filed: Sep. 23, 1977

[51] Int. Cl.² ............................................... A61F 5/02
[52] U.S. Cl. ............................... 128/78; 128/DIG. 20
[58] Field of Search ................. 128/78, 89 R, DIG. 20

[56] References Cited

U.S. PATENT DOCUMENTS

| | | | |
|---|---|---|---|
| 1,646,590 | 10/1927 | Mildenberg | 128/DIG. 20 |
| 2,240,308 | 4/1941 | Mahe | 128/DIG. 20 |
| 3,071,133 | 1/1963 | Eisen | 128/78 |
| 3,955,565 | 5/1976 | Johnson, Jr. | 128/89 R |

Primary Examiner—John D. Yasko
Attorney, Agent, or Firm—John S. Roberts, Jr.

[57] ABSTRACT

A therapeutic corset which is peculiarly adapted for the sacro-lumbar region of the body is disclosed. The corset appliance includes one or more inflatable cell structures which are detachable from the corset and positionally adjustable therein. Different cells have differently sized and configured air pockets, and, as a result of the interchangeability of the cells as facilitated by their ready detachment from the corset, different therapeutic results may be achieved, depending upon the particular cell chosen. The cells are fabricated from a plastic vinyl material which exhibits a low coefficient of stretchability, and, in addition, the inflated configuration of the cell is memorized into the cell structure. Consequently, upon inflation of the cell, the same always assumes substantially the same configuration whereby precisely located counterpressure may be applied to particular areas of the lumbar region of the body.

13 Claims, 15 Drawing Figures

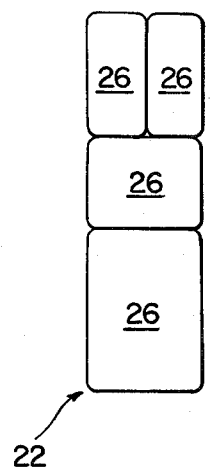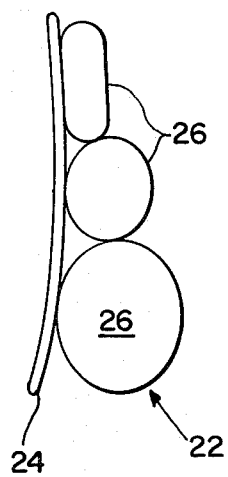
FIG. 3A  FIG. 3B
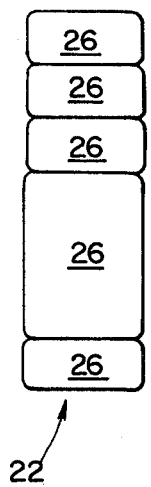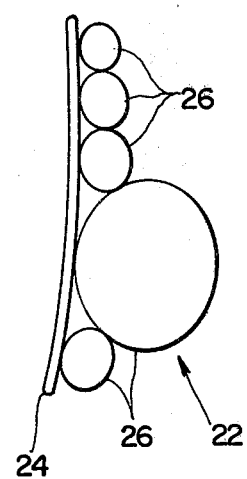
FIG. 4A  FIG. 4B
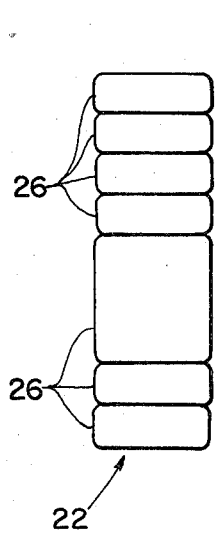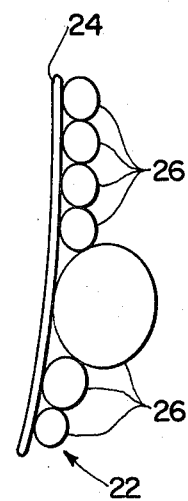
FIG. 5A  FIG. 5B
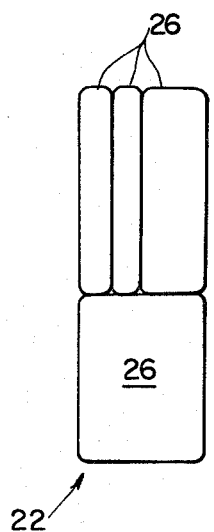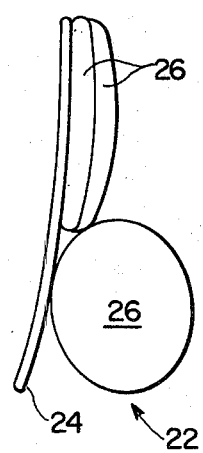
FIG. 6A  FIG. 6B

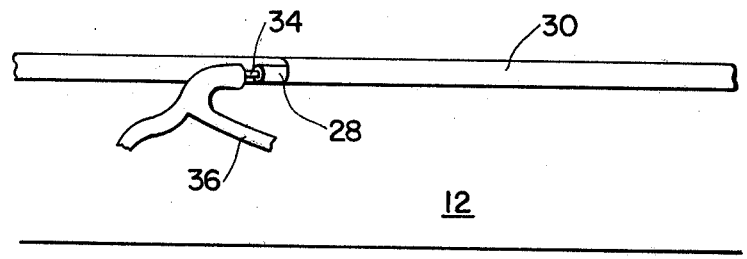
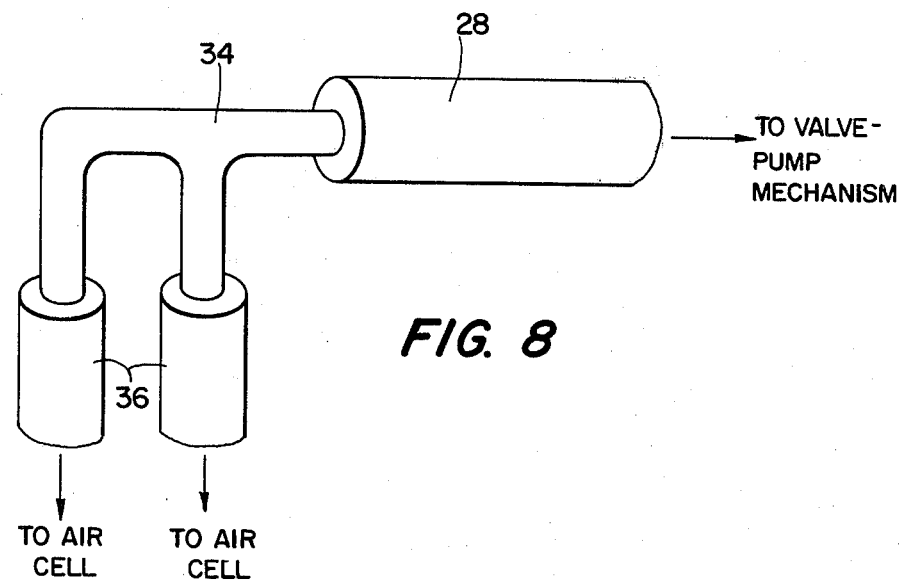
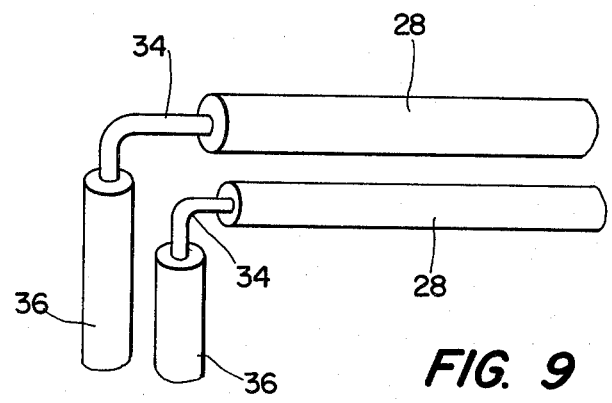

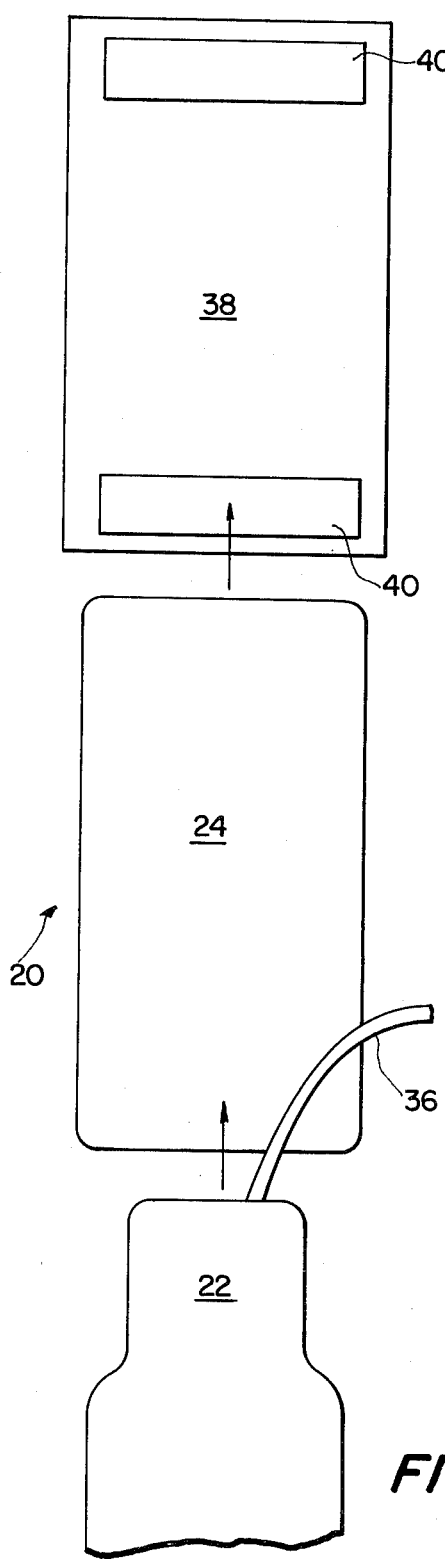
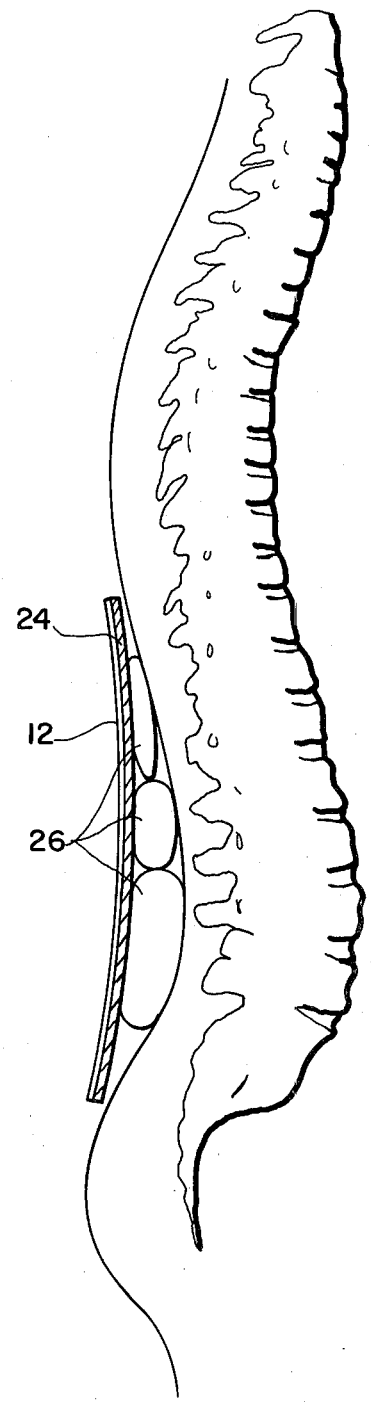
FIG. 10
FIG. 11

THERAPEUTIC CORSET

FIELD OF THE INVENTION

The present invention relates generally to therapeutic devices and more particularly to a corset appliance which may be applied to the sacro-lumbar region of the human body in order to prevent or treat injuries to the aforenoted region.

BACKGROUND OF THE INVENTION

As is well known, the human spine or spinal column is comprised of seven cervical vertebrae, twelve thoracic vertebrae, and five lumbar vertebrae. The vertebrae are disposed in a stacked array and interposed between the same are fibrocartilages or discs. Thirty-one pairs of spinal nerves are also associated with the spinal column, and the nerves are sometimes adversely affected by means of the relative disposition of one or more vertebrae whereby severe pain results. For example, an accident, fall, uneven stress, tension, over-exertion, or the like, can cause a minor displacement or misalignment of one or more of the vertebrae which, in turn, can cause pressure to be exerted upon spinal nerve roots.

It has additionally been found that if the particular misaligned vertebrae is re-aligned in conjunction with the residual, properly aligned vertebrae, the pressure upon the spinal nerves is alleviated and, consequently, the pain suffered by the patient is relieved. The re-alignment of the misaligned vertebrae is normally accomplished as a result of pressure being applied to the particularly afflicted areas of the body and, in accordance with these principles, prior art therapeutic appliances have been developed in order to attempt to provide such counter-pressure to the affected body regions.

Prior art appliances of the aforenoted type are exemplified by those disclosed in U.S. Pat. No. 3,071,133 issued to M. E. Eisen and French Patent No. 1,461,408 issued to M. Gross. The appliances include an inflatable bladder which seeks to exert the aforenoted counter-pressure upon the afflicted body portions as a result of the inflated expansion thereof; however, it has been found that such devices do not and cannot exert the desired counter-pressure at the precise body location as required. This is particularly characteristic, for example, of appliances applied to the lumbar region of the body, or lower back, which, due to its peculiar curvature, usually does not receive adequate contact and pressurization from the appliance.

Still further, when such prior art appliances are normally employed, adequate contact and pressurization of the afflicted body region is attempted to be accomplished by means of increased tightening of the appliance about the wearer's body or increasing the degree of pressurization of the bladder. Such modes of practice may be non-therapeutic as other portions of the body are deleteriously affected. More particularly, as a result of the elastic properties of such bladder devices wherein the bladders have a high coefficient of stretchability, as the pressure within the bladders is increased, the contact area defined between the bladder and the body is increased and the cardio-vascular network of the body is severely constricted in a manner similar to that accomplished by means of a conventional blood pressure cuff. Prolonged usage of such appliances can therefore result in major complications, such as, for example, renal ischemia, muscle spasms, arteriosclerosis-related problems, and even gangrene.

OBJECTS OF THE INVENTION

Accordingly, it is an object of the present invention to provide a new and improved therapeutic appliance.

Another object of the present invention is to provide a new and improved therapeutic appliance which is adapted to be applied to the lumbar region of the human back in order to relieve lower back pain afflictions.

Still another object of the present invention is to provide a new and improved therapeutic appliance for relieving pain within the sacro-lumbar region of the human back and which overcomes the various disadvantages characteristic of prior art appliances.

Yet another object of the present invention is to provide a new and improved therapeutic appliance which is adapted to be applied to the sacro-lumbar region of the human back in order to apply precisely localized counter-pressure to specifically afflicted areas of the aforenoted back region.

Still yet another object of the present invention is to provide a new and improved therapeutic appliance which is adapted to be applied to the sacro-lumbar region of the human back and which is peculiarly capable of being accommodated within the aforenoted region characterized by its unique curvature.

A further object of the present invention is to provide a new and improved therapeutic appliance which employs a plurality of inflatable air cells wherein the configurations of the cells, the number of cells employed, and the relative positions of the cells can be selectively varied so as to achieve optimum counter-pressure conditions.

SUMMARY OF THE INVENTION

The foregoing and other objectives are achieved in accordance with the present invention through the provision of a therapeutic corset appliance which comprises one or more inflatable cell structures which are detachable from the corset and positionally adjustable within the corset. Different cells have differently sized and configured pockets and, as a result of the interchangeability of the cells as facilited by their ready detachment from the corset, different therapeutic results may be achieved, depending upon the particular cell chosen. Each of the cells is fabricated from a plastic vinyl material which exhibits a low coefficient of stretchability and, in addition, the inflated configuration of the cell is memorized into the cell structure. Consequently, upon inflation of the cell, the same always assumes substantially the same configuration and in this manner precisely located counter-pressure may be applied, for example, to particular areas of the lumbar region of the body.

BRIEF DESCRIPTION OF THE DRAWINGS

Various other objects, features, and attendant advantages of the present invention will be more fully appreciated as the same becomes better understood from the following detailed description when considered in conjunction with the accompanying drawings, and therein:

FIGS. 3A–6B are additional embodiments of air cells which may be employed within the appliances of FIGS. 1 and 2;

FIGS. 7 and 8 are different embodiments of air tubing systems which may be employed within the appliance of FIG. 1;

FIG. 9 is a detailed view of the air tubing system which may be employed within the appliance of FIG. 2;

FIG. 10 is an exploded view of another embodiment of the inflatable cell assembly utilized within the corset appliances of FIGS. 1 and 2; and FIG. 11 is a schematic view, partly in cross-section, of an appliance as applied to the lumbar region of the body.

DETAILED DESCRIPTION OF THE ILLUSTRATED EMBODIMENTS

Figure 1:
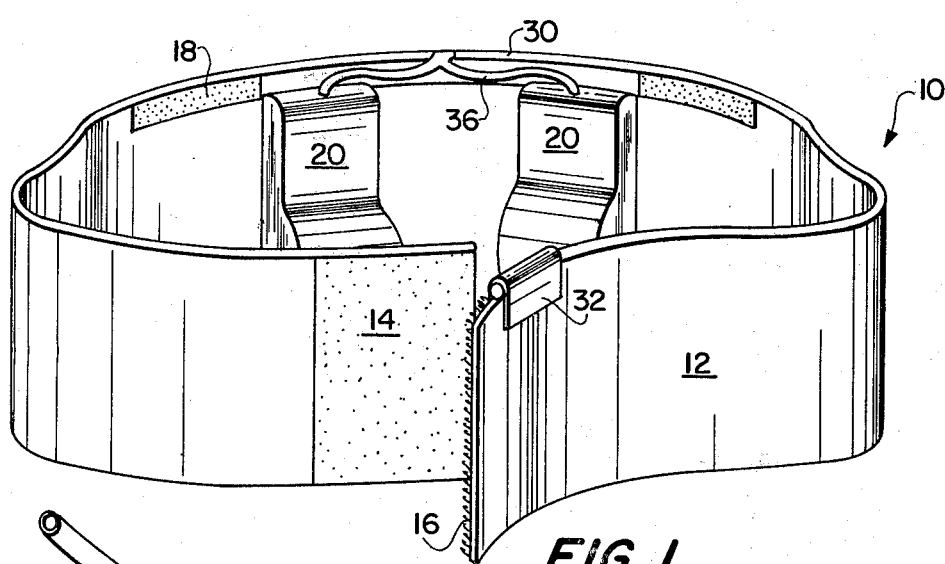
FIG. 1 is a perspective view of a first embodiment of a corset appliance constructed in accordance with the present invention and showing its cooperative parts.

Referring now to the drawings and more particularly to FIG. 1 thereof, the corset appliance of the present invention is generally indicated by the reference character 10. The corset comprises a two-ply fabric laminate 12 and the free ends thereof are provided with suitable fastening means, such as, for example, VELCRO pile 14 and loops 16, whereby the corset may be secured about the wearer's torso with the fastening means disposed within the abdominal area.

Figure 2:
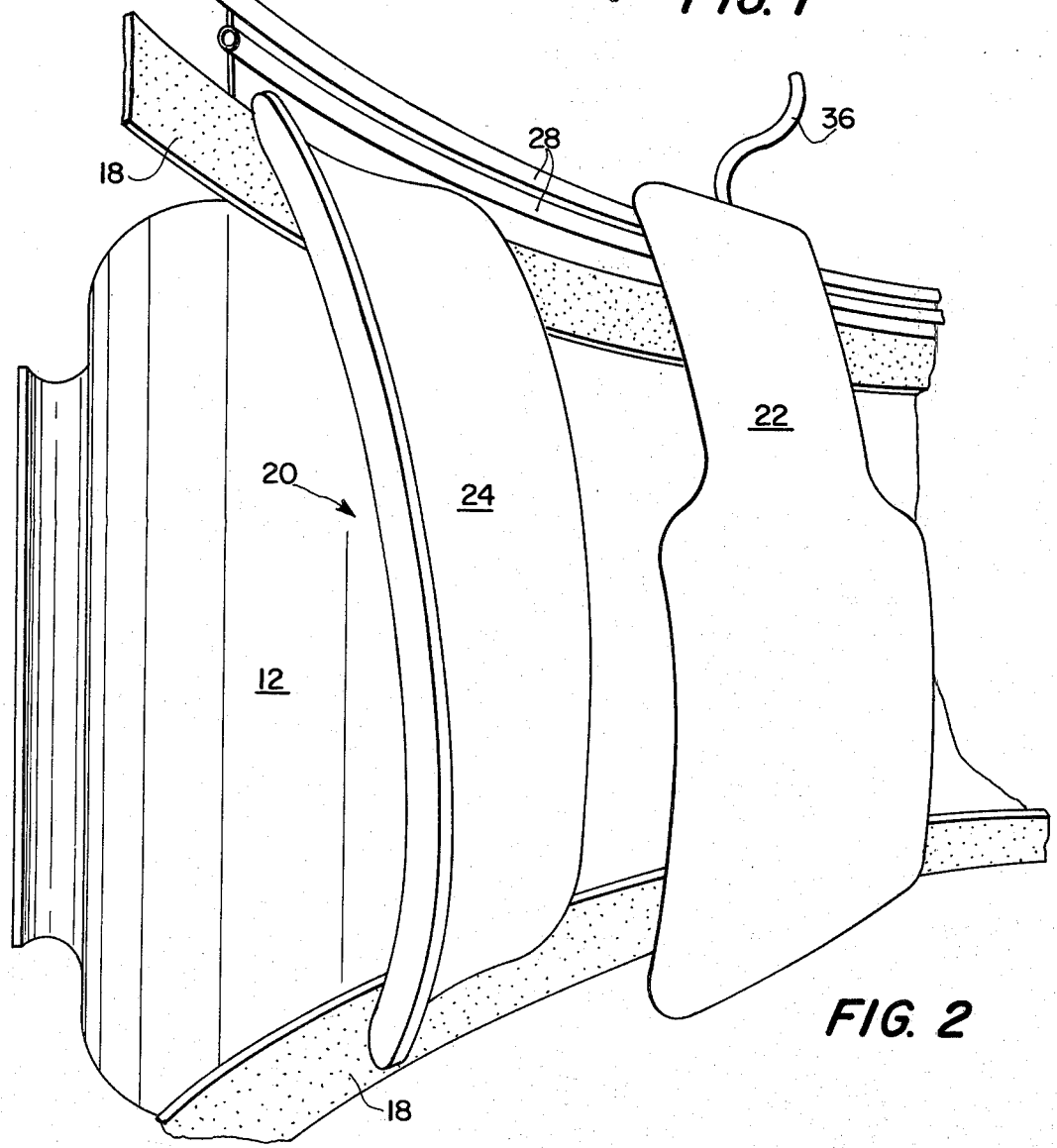
FIG. 2 is a partial perspective view of the appliance shown in FIG. 1 with a modified transfer tube system incorporated therein.

Laterally extending VELCRO tapes or strips 18 are suitably secured to the rear interior surface of the corset within the vicinity of the upper and lower edges thereof and a plurality of vertically extending inflatable air cell assemblies, generally indicated by the reference character 20, are removably secured to the VELCRO strips 18 so as to be supported upon the corset 12. As best seen in FIGS. 2 and 3, the air cell assemblies comprise an inflatable cell 22 which is fabricated of a suitable synthetic plastic, vinyl material whereby, when the cell is deflated, the same assumes a substantially flattened state; however, when the cell is inflated, the same assumes a substantially cylindrical configuration. The cell material is also characterized by a low coefficient of stretchability and the inflated configuration of the cell is memorized into the cell structure. Consequently, the cell always obtains substantially the same configuration upon inflation thereof and such configuration is substantially retained regardless of the pressurized conditions within the cell or external pressures applied thereto. These features are critical to the precise application of counter-pressure to particular portions of the wearer's body, as will become more apparent hereinafter.

With reference being made to FIG. 2, each of the cells 22 is adapted to be mounted upon a vertically disposed rigid support or stay 24 which may be fabricated of a suitable synthetic plastic material and it is additionally noted that the stay is arcuately contoured, both longitudinally and laterally, so as to be appropriately accommodated within the sacro-lumbar region of the body. The cell may be secured to the stay 24 by means of a suitable adhesive and the stay 24 is, in turn, provided with VELCRO fastening means, not shown, upon the rear surface thereof within the vicinity of its upper and lower edges. In this manner, the cell assemblies 20 are removably or detachably mounted within the corset appliance as a result of the fastening procedure accomplished between stays 24 and corset strips 18. As will therefore be appreciated, the cell assemblies may be disposed at selected positions along strips 18 so as to be precisely located relative to particular regions of the sacro-lumbar area of the body. In addition, particularly configured cells 22 may be replaced by differently configured cells 22 in order to optimize the application of the counter-pressure to particularly desired areas of the lumbar region.

More particularly, while cells 22 are generally shown in FIGS. 1 and 2 as comprising single-pocket inflatable structures, the cells may alternatively comprise multiple-pocket structures as disclosed in FIGS. 3A–6B. In fabricating these cells, each of the multiple pockets 26 is formed by heat-sealing together precisely selected portions of a single-pocket cell. As a result, each of the multiple-pocket cells 22 may have selectively different configurations which can include a combination of horizontally and vertically disposed pockets as seen in FIGS. 3A and 3B and FIGS. 6A and 6B, or horizontally disposed pockets of different sizes as seen in FIGS. 4A and 4B, and FIGS. 5A and 5B, and it is, of course, understood that additional permutations and combinations are possible as required for the provision of specific pressure differentials and contact points when the cells are incorporated within the appliance for use within the lumbar region of the back.

In order to provide for the inflation of the cells 22, an air conduit or transfer tube 28 may be interposed between the fabric plies of the corset and may, more particularly, be incorporated into the upper finishing edge or band structure 30 of the corset, as best seen in FIGS. 1 and 7. One end of the transfer tube 28 is adapted to be operatively connected to a suitable valve mechanism 32 which, in turn, is adapted to be connected to a suitable air source, such as, for example, a squeeze bulb similar to that shown in the aforenoted Eisen and Gross patents. The other end of the transfer tube 28 is adapted to project out of the band 30 and be connected to an adaptor tube 34 which facilitates, in turn, the fluidic communication between transfer tube 28 and the access tubing 36 which leads to the air cells 22.

As seen in FIGS. 1 and 7, a pair of cells may be connected to the transfer tube 28 by means of an adaptor tube 34, having a single inlet and a single outlet, and a single, branched access tube 36. Such an arrangement is adequate when it is predetermined that the pair of cells 22 will always be utilized together within the corset. However, when it is possible that one of the cells 22 is to be replaced by a differently configured cell, such as, for example, one of the cells disclosed in FIGS. 3A–6B, the tubing arrangement of FIG. 8 is preferred. In accordance with the latter embodiment, a branched adaptor tube 34, having a single inlet end and a multiple outlet end, is interposed between the transfer tube 28 and individual access tubes 36 separately connected to the individual cells 22. As a result of this arrangement, any particular cell 22 may be removed from the corset merely by disconnecting the cell access tube 36 from the branched adaptor 34, replacing the cell with a different cell, and connecting the access tube 36 of the new cell with the free branch of the adaptor tube 34.

Referring again to FIG. 2, it will be noted further that in lieu of the single transfer tube 28 disclosed in the embodiments of FIGS. 1 and 7, a plurality of transfer tubes 28 may be incorporated within the corset appliance and it will be appreciated that the valved ends of the tubes 28 are each provided with valve mechanisms, not shown, for separate connection to the air source, not shown. The other ends of the transfer tubes 28 are adapted to be individually and separately connected to the individual access tubes 36 of the cells 22, and in this manner, the separate cells 22 may be inflated to different pressures. This embodiment therefore provides even greater control and utilization of the inflatable cells for their therapeutic purposes. In connecting the multiple transfer tubes 28 to the cells 22, it is seen that individual adaptor tubes 34, similar to that employed within the embodiment of FIG. 7, may be utilized between the tubes 28 and the individual access tubes 36 of the air cells, as best seen in FIG. 9.

Considering now FIG. 10, a further embodiment of the cell assembly 20 is disclosed. As compared to the embodiment employed within the appliance as disclosed in FIG. 2, in lieu of the air cell 22 being adhesively bonded to the rigid plastic stay 24 and the latter fastened to the corset 12 by means of VELCRO stripping, the air cell 22, in accordance with the embodiment of FIG. 10, may simply be mounted upon the stay 24, and the cell-stay assembly may then be inserted within a knitted fabric stocking tube 38. Both ends of the tube 38 are initially open and the rear surface thereof is provided with VELCRO strips 40 within the vicinity of the upper and lower edges thereof. After insertion of the cell-stay assembly within the tube 38, the lower end thereof may be sewn closed and the upper end thereof likewise sewn closed with the exception of an aperture, not shown, through which the air cell access tube 36 projects outwardly. The entire assembly may then be removably fastened to the corset as a result of the fastening interaction defined between the VELCRO strips 18 and 40 of the corset and tube, respectively.

In utilizing the corset appliance of the present invention, the same is initially secured about the torso of the wearer with the fastening means 14–16 covering the abdominal area of the body while the inflatable cell structures are disposed within the lumbar region of the body. As disclosed in FIG. 11, the particular cell structure 22 may, for example, be similar to that disclosed in FIGS. 3A and 3B with a plurality of different sized horizontally disposed air pockets 26 in combination with a plurality of vertically disposed pockets 26.

As a result of the unique fabrication of the air pockets 26, as well as the particular memory plastic material utilized in initially fabricating the cell 22, as noted hereinabove, it is seen that upon inflation of the cell 22 and the pockets 26, the pockets attain predetermined diametrical dimensions so as to be precisely accommodated within the uniquely curved lumbar region of the back. The contact area defined between the pockets 26 and the back is relatively small and is dependent upon the degree of pressurization within the cell and pockets. Contrary to the pressurization of conventional bladders, however, as the pressurization of the cells 22 is increased, the contact area between the cells and the back decreases and the counter-pressure exerted upon the back by means of the cells increases. With conventional bladders, the contact areas increase with corresponding increases in pressure and severe constriction of the cardio-vascular system results. Consequently, precisely controlled therapeutic results are obtained with the appliance of the present invention without concomitant dangerous effects being imposed upon the wearer's body.

Thus, it may be seen that the appliance of the present invention has important advantages over known prior art devices in view of the fact that precisely located areas of counter-pressure are able to be developed and defined with respect to particular regions of the body in order to impart therapy thereto. It is to be noted that while only two cell structures have been disclosed within the appliance of the present invention, it is, of course, possible that more than two, or only one, of such cells can be utilized in accordance with the particular therapy desired or required. When employing an even number of the cells, it is usually the practice that an equal number of the same will be disposed upon opposite sides of the spinal column and, when employing an odd number of cells, it is normally the practice to dispose an equal number of the cells upon opposite sides of the spinal column and one cell directly applied to the spinal column. Of course, for particular therapeutic purposes, these arrangements may be varied and, in addition, the pressure within a particular cell may be greater than that within a different cell.

Obvious, additional modifications and variations of the present invention are possible in light of the above teachings. It is, therefore, to be understood that within the scope of the appended claims, the present invention may be practiced otherwise than as specifically described herein.

What is new and desired to be secured by Letters Patent of the United States is:

1. A therapeutic appliance for application to the sacro-lumbar region of the human body comprising:
   a band-like support means having free ends and a length sufficient to extend around the back and encircle the abdominal region of the body;
   releasable connecting means embodied with free ends of said support means to secure the same in position;
   at least one inflatable air cell means; and
   releasable cooperating fastening means operably related between said air cell means and the surface of said support means that faces and extends across the sacro-lumbar region of the human body for releasably and adjustably positioning said air cell means within said suport means.

2. A therapeutic appliance as claimed in claim 1 in which said at least one inflatable air cell means includes a plurality of differently sized and configured intercommunicating air-holding pockets so as to apply precisely located counter pressure to selected particular areas of the lumbar region of the body.

3. A therapeutic appliance as claimed in claim 1 and said air cell means comprising a plurality of inflatable air cell means removably and adjustably positioned within said support means.

4. A therapeutic appliance as claimed in claim 1 and a rigid stay arranged between said air cell means and said support means.

5. A therapeutic appliance as claimed in claim 4 and said rigid stay means having an arcuate contour extending both longitudinally and transversely of its surface.

6. A therapeutic appliance as claimed in claim 5 and means interconnecting said air cell means and said rigid stay means in unitary relationship.

7. A therapeutic appliance as claimed in claim 6 and the means interconnecting said air cell means and said rigid stay means comprising a fabric casing surrounding and enclosing said rigid stay means and part of said cooperating fastening means being arranged on said fabric casing.

8. A therapeutic appliance as claimed in claim 1 in which said inflatable air cell means includes a plurality of different sized and configured intercommunicating air-holding pockets, said air cell means being of a plastic vinyl material having a low coefficient of stretchability with the inflated configuration of the pockets being memorized into said plastic vinyl material whereby upon inflation substantially the same configuration of said pockets is always obtained so as to apply precisely located counter pressure to selected particular areas of the lumbar region of the body, and air-conveying conduit means carried by said support means and interconnected with said air cell means for inflating said air cell means.

9. A therapeutic appliance as claimed in claim 8 in which said air cell means includes a plurality of air cell means each including a plurality of different sized and configured intercommunicating air-holding pockets.

10. A therapeutic appliance as claimed in claim 9 in which said air-holding pockets comprise a combination of pockets having their major axes extending respectively transversely of and longitudinally of said support means.

11. A therapeutic device as claimed in claim 9 in which said air holding pockets comprise a combination of pockets having their major axes extending transversely of said support means.

12. A therapeutic appliance as claimed in claim 1 and said air cell means comprising a plurality of air cell means and each of said connecting means and fastening means including Velcro type fasteners.

13. A therapeutic appliance as claimed in claim 1 and said air cell means comprising a plurality of air cell means each having a plurality of intercommunicating differently therapeutically designed air-holding pockets for removably and changeably positioning within said support means in accordance with therapeutic purposes, air conduit means carried by said support means and including an end portion adapted to be connected to a source of air, said air cell means including access tubing means and adaptor tubing means interconnecting said air conduit means and said access tubing means.

* * * * *